(12) United States Patent
    Alzaga

(10) Patent No.: US 12,605,207 B2
(45) Date of Patent: Apr. 21, 2026

(54) SYSTEM FOR DISPLAYING AN AUGMENTED REALITY AND METHOD FOR GENERATING AN AUGMENTED REALITY

(71) Applicant: Siemens Healthcare GmbH, Erlangen (DE)

(72) Inventor: Amilcar Alzaga, Schönbrunn im Steigerwald (DE)

(73) Assignee: Siemens Healthineers AG, Forchheim (DE)

( * ) Notice: Subject to any disclaimer, the term of this patent is extended or adjusted under 35 U.S.C. 154(b) by 1172 days.

(21) Appl. No.: 17/376,310

(22) Filed: Jul. 15, 2021

(65) Prior Publication Data

US 2022/0022964 A1      Jan. 27, 2022

(30) Foreign Application Priority Data

Jul. 21, 2020    (EP) .................................... 20187042

(51) Int. Cl.
| | |
|---|---|
| *G06F 30/20* | (2020.01) |
| *A61B 34/10* | (2016.01) |
| *A61B 34/20* | (2016.01) |
| *A61B 90/00* | (2016.01) |
| *G02B 27/01* | (2006.01) |

(52) U.S. Cl.
    CPC .............. *A61B 34/10* (2016.02); *A61B 34/20* (2016.02); *A61B 90/36* (2016.02); *G02B 27/017* (2013.01); *A61B 2034/102* (2016.02); *A61B 2034/107* (2016.02); *A61B 2034/2051* (2016.02); *A61B 2034/2055* (2016.02); *A61B 2034/2063* (2016.02); *A61B 2034/2065* (2016.02); *A61B 2034/2068* (2016.02); *A61B 2090/365* (2016.02)

(58) Field of Classification Search
    CPC ... A61B 34/10; A61B 34/20; A61B 2034/102; A61B 2034/107; A61B 2034/2051; A61B 2034/2055; A61B 2034/2063; A61B 2034/2065; A61B 2034/2068; A61B 2090/365; A61B 90/36
    USPC .......................................................... 703/20
    See application file for complete search history.

(56) References Cited

U.S. PATENT DOCUMENTS

| | | | |
|---|---|---|---|
| 9,524,585 B2 * | 12/2016 | Steed .................... | G06T 19/006 |
| 2019/0053855 A1 * | 2/2019 | Siemionow .............. | G06T 5/70 |

(Continued)

OTHER PUBLICATIONS

Dr. Maddalena Strumia, et al. Anatomical Deformation Estimation Based on Subcutaneous Markers, Mar. 21, 2019, abstract.

(Continued)

*Primary Examiner* — Andre Pierre Louis
(74) *Attorney, Agent, or Firm* — Lempia Summerfield Katz LLC

(57) ABSTRACT

A system and method for displaying an augmented reality including a medical device for acquiring image data, a first display device for displaying the image data, a first tracking element for locating the medical device, and a second tracking element for locating the first and a second display device. The system is configured to receive a planning dataset and generate the augmented reality based on the planning dataset and a spatial positioning of the medical device. The planning dataset is spatially arranged with respect to the first display device according to detected spatial positionings of the first and second display device. The second display device is configured for displaying the augmented reality.

18 Claims, 7 Drawing Sheets

(56) References Cited

U.S. PATENT DOCUMENTS

| | | | |
|---|---|---|---|
| 2020/0036910 A1 | 1/2020 | Alzaga et al. | |
| 2020/0066054 A1* | 2/2020 | Yin | G02B 27/017 |
| 2020/0234449 A1 | 7/2020 | Regensburger et al. | |
| 2021/0137605 A1* | 5/2021 | Samadani | G16H 40/63 |
| 2021/0327303 A1* | 10/2021 | Buras | A61B 8/467 |
| 2022/0296803 A1* | 9/2022 | Leroy | A61M 1/84 |

OTHER PUBLICATIONS

European Search Report for European Application No. 20187042. 5-1126 dated Jan. 19, 2021.

* cited by examiner

SYSTEM FOR DISPLAYING AN AUGMENTED REALITY AND METHOD FOR GENERATING AN AUGMENTED REALITY

CROSS REFERENCE TO RELATED APPLICATION

This application claims the benefit of EP 20187042.5 filed on Jul. 21, 2020, which is hereby incorporated by reference in its entirety.

FIELD

Embodiments relate to a system for displaying an augmented reality and a method for generating an augmented reality.

BACKGROUND

For supporting a medical staff, for example a physician, during an examination and/or treatment of a subject, for example intra-procedurally, often times pre-procedural medical images of the subject are used for planning and/or displayed to the medical staff. A highly realistic visualization of such medical images may be achieved by displaying an augmented reality (AR). In augmented reality applications real objects, for example the subject, may be overlaid with virtual data and observed by the medical staff. However, a realistic display of the augmented reality often requires a precise registration within the virtual data and/or between the virtual data and the subject, that may be complicated by subject motion.

Alternatively, medical devices, for example a catheter and/or endoscope and/or laparoscope, may be used by the medical staff to intra-procedurally acquire, for example real-time, image data from a region under examination. Adversely, existing medical devices, for example rigid and/or articulated endoscopes, frequently lack the ability of changing a field-of-view and/or the ability of being optically, for example visually, tracked.

Furthermore, there are medical devices that may be configured to acquire three-dimensional (3D) image data from the region under examination, for example via a stereoscopic lens. However, the medical devices often possess only a small stereoscopic baseline. The depth perception may be significantly less than the perception of human eyes. A missing or only small depth cue information with regard to the intra-procedural image data may significantly complicate a precise actuation of the medical device by the medical staff.

Moreover, changes and/or modifications to the intra-procedural medical images often require a processing of a video signal originating from the medical device. Adversely, this processing of the video signal may result in a noticeable time lag between the acquisition of the intra-procedural image data and its display, that may hamper a precise actuation of the medical device during the examination and/or treatment, for example minimally invasive surgery.

BRIEF SUMMARY AND DESCRIPTION

The scope of the present disclosure is defined solely by the appended claims and is not affected to any degree by the statements within this summary. The present embodiments may obviate one or more of the drawbacks or limitations in the related art.

Embodiments provide depth cue information and/or pre-processed information and/or planning information to support a user intra-procedurally.

Embodiments provide a system for displaying an augmented reality. The system includes a controller, a first display device, a second display device, a first tracking element, a second tracking element, and a medical device. The medical device is configured to acquire image data of a region under examination of a subject and provide the image data to the first display device. In addition, the first display device is configured to display a graphical representation of the image data. The first tracking element is configured to detect a spatial positioning of the medical device. The second tracking element is configured to detect spatial positionings of the first display device and the second display device. In addition, the system is configured to receive a planning dataset. The system is further configured to generate the augmented reality based on the planning dataset and the detected spatial positioning of the medical device. The planning dataset is spatially arranged with respect to the first display device in accordance with the detected spatial positionings of the first and second display device. In addition, the second display device is configured to display a graphical representation of the augmented reality.

The medical device may include a diagnostic and/or surgical device that may be configured to acquire, for example intra-procedural and/or real-time, image data of the region under examination of the subject. The subject may be a human patient and/or an animal patient and/or a phantom. For example, the medical device may include a catheter and/or endoscope and/or laparoscope, that may be configured to be at least partially placed inside the region under examination of the subject. The region under examination of the subject may include an anatomical region and/or a hollow organ and/or body cavity of the subject. For example, the medical device may include an optical and/or electro-magnetic and/or ultrasound sensor, that may be configured to capture the image data of the region under examination. The medical device may be configured to passively and/or actively acquire the image data. In the first case, the medical device may be configured to capture the image data. In the second case, the medical device may further include a source, for example an optical source and/or fiber and/or an electromagnetic source and/or an ultrasound transducer, that may be configured to emit light and/or electromagnetic and/or ultrasonic waves. The sensor and source may be spatially arranged next to each other. Alternatively, the sensor and source may be spatially arranged apart from each other, for example the source or sensor may be placed adjacent to and/or outside the region under examination. The medical device may further include a medical device interface, that may be configured to provide the image data to the first display device.

The image data may include a two-dimensional (2D) and/or three-dimensional (3D) representation of at least part of the region under examination. In addition, the image data may be time-resolved. The image data may further include metadata. The metadata may include an information regarding an acquisition geometry and/or operating parameter of the medical device.

The first display device may include a monitor and/or display, that may be configured to display the graphical representation of the image data. The first display device may be configured to display the graphical representation of the image data in real-time.

The first tracking element may include a sensor, for example an electromagnetic and/or optical and/or ultrasound sensor, that may be configured to detect a spatial positioning of the medical device. The first tracking element may be configured to detect and/or track and/or monitor the spatial positioning, for example a spatial position and/or orientation, of the medical device, for example in a coordinate frame of the subject and/or a reference coordinate frame. The medical device may include a first marker element, that may be identified and spatially located by the first tracking element. The first marker element may be configured as a predefined shape and/or contour and/or segment of the medical device, for example a fiducial marker and/or a predefined segment of the medical device. The first marker element may be configured as at least one marker object that may be attached to the medical device, for example on a distal and/or proximal portion of the medical device. For example, the first tracking element may include a camera, for example a mono and/or stereo camera, that may be configured to detect and/or track and/or monitor the medical device, for example the first marker element.

The first tracking element may be at least partially integrated in and/or attached to the medical device. In addition, the first tracking element may include an acceleration and/or inertia and/or position sensor, for example a gyroscope. When the first tracking element is at least partially integrated in and/or attached to the medical device, the spatial positioning of the medical device may be detected and/or tracked without the first marker element.

Analogously, the second tracking element may include a sensor, an electromagnetic and/or optical and/or ultrasound sensor, that may be configured to, for example simultaneously, detect a spatial positioning of the first and second display device. Alternatively, the second tracking element may include a first and a second sensor. The first sensor may be configured to detect the spatial positioning of the first display device and the second sensor may be configured to detect the spatial positioning of the second display device. For example, the second tracking element may be configured to detect and/or track the spatial positioning, for example a spatial position and/or orientation, of the first and second display device, for example relative to each other and/or in a common coordinate frame. The second tracking element may be configured to detect the spatial positionings of the first and second display element in the same reference coordinate frame in which the spatial positioning of the medical device is detected.

The first display device may include a second marker element and/or the second display device may include a third marker element. The second tracking element may be configured to identify and spatially locate the second and/or the third marker element. The second marker element may be configured as a predefined shape and/or contour and/or segment of the first display device, for example a fiducial marker. The second marker element may be configured as at least one marker object that may be attached to the first display device. Analogously, the third marker element may be configured as a predefined shape and/or contour and/or segment of the second display device, for example a fiducial marker. The third marker element may be configured as at least one marker object that may be attached to the second display device. The second tracking element may include a camera, for example a mono and/or stereo camera, that may be configured to detect and/or track the first and/or second display device, for example the second and/or the third marker element.

The second tracking element may be configured to detect a relative and/or absolute spatial positioning between the first and second display device. By way of example, the first and/or the second display device may include a sensor, for example an acceleration and/or inertia and/or position sensor, that may be configured to detect and provide the spatial positioning, for example the spatial position and/or orientation, of the respective display device to the second tracking element. This may be particularly helpful, if an obstacle occurs in a line-of-sight between the second tracking element and the first and/or second display device.

The system may include a system interface, that may be configured to receive the planning dataset, for example via a wired and/or wireless transmission from a medical imaging system and/or a processing unit. The system interface may be configured to collect and/or readout data from an electronically readable storage medium and/or to receive data from a memory unit, for example a database. The medical imaging system may be configured to acquire the planning dataset of the subject, for example pre-procedurally. The planning dataset may include a 2D and/or 3D representation of at least part of the region under examination of the subject. In addition, the planning dataset may be time-resolved. The planning dataset may further include pre-processed information, for example annotations and/or anatomical landmarks and/or geometrical landmarks and/or enhanced features, for example depth cue information. In addition, the planning dataset may include planning information regarding a path for a medical object, for example the medical device, and/or information regarding a treatment plan. The planning dataset may at least partially include a representation of the region under examination where the medical device is placed and/or that is represented in the image data. Hence, the image data and the planning dataset may each include a representation of at least a common part of the region under examination. The planning dataset may further include metadata. The metadata may include an information regarding an acquisition geometry and/or operating parameter of the medical imaging system during the acquisition of the planning dataset. For example, the metadata may include an information regarding a spatial reference and/or registration with regard to the subject coordinate frame.

The medical imaging system for acquiring and/or providing the planning dataset may be a medical X-ray system, for example a C-arm X-ray system, and/or a computed tomography system (CT) and/or a magnetic resonance imaging system (MRI) and/or a positron emission tomography system (PET) and/or an ultrasound imaging system. The medical imaging system may be configured to provide the planning dataset to the system, for example via the system interface. The medical imaging system for acquiring and/or providing the planning dataset may be a same or a different imaging modality than the medical device.

The system may be further configured to generate the augmented reality based on the planning dataset and the detected spatial positioning of the medical device. The augmented reality may include a 2D and/or 3D graphical representation of the planning dataset. The system may be configured to generate the graphical representation of the planning dataset based on a characteristic of the medical device, for example a type and/or operating parameter and/or an acquisition parameter, and/or the detected spatial positioning of the medical device. By way of example, the graphical representation of the planning dataset may include depth cue information. By way of example, the depth cue information may include a color shading and/or virtual shadows and/or virtual light effects and/or blurring and/or enhanced geometric features. In addition, the system may be configured to generate the graphical representation of the planning dataset such that the graphical representation of the planning dataset matches at least partially with a field-of-view of the medical device. For this purpose, the system may be configured to transform, for example rotate and/or translate and/or scale and/or deform and/or truncate, the planning dataset based on the detected spatial positioning and/or the characteristic of the medical device.

The second display device may be portable and/or wearable by a user. In addition, the second display device may be configured to display the graphical representation of the augmented reality (abbreviated: AR). The second display device may be configured to be at least partially transparent. The second display device may be configured to be worn by the user at least partially within a field-of-view of the user. The second display device may be configured to display a stereoscopic view of the augmented reality, for example the graphical representation of the augmented reality, to the user. Hereby, the user may perceive the depth cue information from the augmented reality, for example the graphical representation of the planning dataset, that may support the user in real-time when actuating the medical device intra-procedurally.

The second display device may include a second display interface, that may be configured to receive the augmented reality, for example via a wired or wireless transmission from the processing unit. The second display interface may be configured to collect and/or readout data from an electronically readable storage medium and/or to receive data from a memory unit, for example a database.

The system may be configured to spatially arrange the planning dataset, for example the graphical representation of the planning dataset, with respect to the first display device in accordance with the detected spatial positionings of the first and second display device. For example, the system may be configured to spatially arrange the graphical representation of the augmented reality including the graphical representation of the planning dataset with respect to the graphical representation of the image data, that is displayed on the first display device. The system may be configured to determine a spatial relation and/or registration between the first display device, that is displaying the graphical representation of the image data, and the second display device, that is displaying the graphical representation of the augmented reality, based on the detected spatial positionings of the first and second display device. The augmented reality, that is displayed by the second display device, may be at least partially overlaid and/or integrated into the graphical representation of the image data, that is displayed by the second display device. The graphical representation of the augmented reality may be immersed into the graphical representation of the image data. At least part of the graphical representation of the augmented reality, for example an anatomical and/or geometrical feature, may be spatially and/or visually matched to the graphical representation of the image data on the first display device. The spatial and/or visual matching of the graphical representation of the augmented reality may include a rotation and/or translation and/or scaling and/or deformation and/or truncation of at least part of the graphical representation of the augmented reality based on the detected relative spatial positioning between the first and second display device. The matching may include an at least regional adaption of an opacity and/or coloring of the graphical representation of the augmented reality, for example based on an image parameter of the image data and/or a display parameter of the first display device.

The system may permit an enhancement of the image data, that is displayed on the first display device, via the graphical representation of the planning dataset in the augmented reality. Consequently, the augmented reality may provide additional depth cue information and/or pre-processed information and/or planning information in an overlay with the image data to the user. For example, the display of the image data on the first display device may remain unaffected and/or unaltered and/or non-delayed by the display of the augmented reality on the second display device.

In an embodiment, the system may be further configured to generate the augmented reality including a virtual representation of the medical device based on the detected spatial positioning of the medical device.

The system may be configured to generate the augmented reality including a 2D and/or 3D arrangement of the planning dataset and the virtual representation of the medical device. For example, the virtual representation of the medical device may include a 2D and/or 3D model of the medical device, that may be generated, for example simulated and/or derived, based on a user input and/or a characteristic and/or an operating parameter and/or an acquisition parameter of the medical device. By way of example, the virtual representation of the medical device may include a volume model, for example a mesh model, and/or a shape model. Alternatively, the virtual representation of the medical device may be selected from a library including virtual representations of different medical devices. The selection may be based on a user input and/or a characteristic of the medical device.

The virtual representation of the medical device may be configured as a realistic and/or simplified, for example abstracted, model of the medical device. A spatial extent and/or shape of the model may at least partially match the spatial extent and/or shape of the medical device. The virtual representation of the medical device may include enhanced geometric features, for example a contour and/or area and/or a longitudinal direction, and/or operating features, for example a planned path and/or a graphical representation of a field-of-view, of the medical device that may improve a visual perception by the user.

In addition, the virtual representation of the medical device may be used to calibrate the field-of-view of the medical device with regard to a specific coordinate frame, for example the coordinate frame of the subject and/or the reference coordinate frame. The system may be configured to calibrate and/or register the field-of-view of the medical device, for example with respect to the augmented reality, by calibrating the field-of-view of the virtual representation of the medical device.

The system may be further configured to spatially arrange the virtual representation of the medical device with respect to the planning dataset based on, for example according to, the detected spatial positioning, for example the spatial position and/or spatial orientation, of the medical device. By way of example, this may be implemented by registering the detected spatial positioning of the medical device and the planning dataset in the subject coordinate frame. The augmented reality may depict the virtual representation of the medical device and the graphical representation of the planning dataset in a virtual spatial arrangement, that may be in accordance with the real spatial arrangement of the medical device with respect to the region under examination of the subject. The system may be configured to at least partially overlay and/or integrate the virtual representation of the medical device and the graphical representation of the planning dataset for generating the augmented reality.

The user may hereby visually perceive the current and/or planned spatial positioning of the medical device with respect to the planning dataset via the augmented reality.

In an embodiment, the system may be further configured to monitor at least one of the detected spatial positionings. In addition, the system may be configured to adapt the augmented reality when a change in the at least one of the detected spatial positionings occurs.

The first and/or second tracking element may be configured to monitor the spatial positionings of the respective device by either continuously or recurrently detecting the spatial positionings, for example according to a predefined time interval. The first and/or second tracking element may further be configured to detect and/or signal a change in the respectively detected, for example monitored, spatial positionings by comparing the current spatial positioning with a previously detected spatial positioning of the respective device. The comparison may include computing a difference between the previously and currently detected spatial positioning and comparing the difference to a predefined threshold. The first and/or second tracking element may be configured to signal the change in the respectively detected spatial positionings when the difference exceeds the predefined threshold. For each of the detected spatial positionings a different predefined threshold may be specified, for example via a user input.

The system may be configured to adapt the augmented reality, for example the graphical representation of the planning dataset and/or the virtual representation of the medical device, when a change in the spatial positioning of the medical device is detected by the first tracking element. Hereby, the adapted augmented reality may depict the graphical representation of the planning dataset and/or the virtual representation of the medical device in the virtual spatial arrangement, that may hence remain in accordance with the real spatial arrangement of the medical device with respect to the region under examination of the subject. The adaption of the augmented reality may include a rigid and/or non-rigid transformation of the graphical representation of the augmented reality, for example the graphical representation of the planning dataset and/or the virtual representation of the medical device. The rigid and/or non-rigid transformation of the graphical representation of the augmented reality may include a rotation and/or translation and/or scaling and/or deformation and/or truncation of at least part of the augmented reality.

The system may be configured to adapt the augmented reality when the second tracking element detects a change in the relative spatial positioning between the first and second display device. If the spatial positionings of the first and second display device are changing uniformly, an adaption of the augmented reality may not become necessary.

When a change in the relative spatial positioning between the first and second display device is detected by the second tracking element, the graphical representation of the augmented reality may be adapted such that it immerses into the graphical representation of the image data displayed by the first display device. The system may be configured to adapt at least part of the graphical representation of the augmented reality such that it spatially and/or visually matches with the graphical representation of the image data, for example an anatomical and/or geometrical feature. The adaption of the at least part of the graphical representation of the augmented reality may include a spatial and/or visual matching of the graphical representation of the augmented reality. The spatial and/or visual matching of the at least part of the graphical representation of the augmented reality may include a rotation and/or translation and/or scaling and/or deformation and/or truncation of the at least part of the graphical representation of the augmented reality based on the detected change in the relative spatial positioning between the first and second display device.

By, for example continuously, adapting the augmented reality when a change in at least one of the detected spatial positionings is detected, an immersive display of the augmented reality and the image data may be ensured. For example, when the second display device is configured as a head-mounted display device, the augmented reality may be adapted whenever the head of the user is moved, and thereby the second display device, with respect to the first display device.

In an embodiment, the second tracking element may be mounted to the second display device in a predefined position. For example, the second tracking element may be attached to and/or at least partially integrated into the second display device such that a relative positioning between the second display device and the second tracking element remains unchanged. The predefined position of the second tracking element with respect to the second display device may permit an inherent registration between the spatial positioning of the second display device and the second tracking element, even when the second display device is moved. The second tracking element may be mounted to the second display device in a stationary predefined position and/or orientation. Thereby, the second tracking element may be configured to detect the spatial positioning of the first display device with respect to the second display device, for example the relative spatial positioning between the two display devices.

In an embodiment, the second tracking element may be arranged spatially apart from the first and second display device.

By way of example, the second tracking element may be mounted to a wall and/or floor and/or ceiling of a room, in which room the first and second display device are located. The second tracking element may be stationary, for example with respect to the room, whilst the first and/or the second display device may be mobile.

By arranging the second tracking element spatially apart from the first and second display device, a physical weight and/or power consumption of the first and second display device may be reduced. In addition, when arranged spatially apart, the second tracking element may be configured to detect spatial positionings of further second display devices, that may be configured likewise to the second display device and may be worn by further users within the same room.

In an embodiment, the system may be further configured to segment at least part of the planning dataset and generate the augmented reality based on the segmented planning dataset.

The system may be configured to segment a predefined anatomical and/or geometrical structure and/or region-of-interest of the planning dataset, for example based on a user input. The segmentation may be based on a comparison between image values of the planning dataset and a predefined image threshold. Alternatively, the segmentation may be based on a shape-based and/or contour-based and/or pattern-based and/or landmark identification algorithm Thereby, the most relevant information from the planning dataset for the current application may be incorporated into the generation of the planning dataset.

In an embodiment, the first tracking element may be configured as a medical imaging system.

For example, the first tracking element may be configured as a medical X-ray system, for example a C-arm X-ray system, and/or a computed tomography system (CT) and/or a magnetic resonance imaging system (MRI) and/or a positron emission tomography system (PET) and/or an ultrasound imaging system. The first tracking element may be configured to, for example recurrently and/or continuously, acquire further medical image data of the region under examination and to detect the spatial positioning of the medical device based on the further medical image data. The first tracking element may be configured to identify and locate the medical device in the further medical image data, for example based on the first marker element. The first tracking element may be configured to identify and spatially locate the first marker element, for example a graphical representation of the first marker element, in the further medical image data. The first marker element may exhibit a spatial structure and/or shape and/or marker structure and/or landmark, that enables a detection of the spatial positioning of the first marker element based on its graphical representation in the further medical image data.

When the first tracking element is configured as a medical imaging system and the planning dataset was acquired by the medical imaging system, the detected spatial positioning of the medical device may inherently be registered to the planning dataset. This may be of particular advantage for the generation of the augmented reality based on the planning dataset and the detected spatial positioning of the medical device.

In an embodiment, the medical imaging system may be configured to acquire a device dataset. In addition, the system may be further configured to segment the medical device in the device dataset and generate the virtual representation of the medical device based on the segmented device dataset.

The further medical image data may include the device dataset. The device dataset may include a graphical representation of the medical device. The device dataset may depict the graphical representation of the medical device including a contour and/or shape of at least part of the medical device. The system may be configured to segment the medical device, for example the graphical representation of the medical device, in the device dataset. The segmentation may be based on a comparison between image values of the device dataset and a further predefined image threshold. Alternatively, the segmentation may be based on a shape-based and/or contour-based and/or pattern-based and/or landmark-based identification algorithm. Alternatively, or in addition, the system may be configured to receive a characteristic of the medical device, for example a type and/or operating parameter and/or an acquisition parameter of the medical device. The segmentation may at least partially be based on the characteristic of the medical device.

The system may be configured to generate the virtual representation of the medical device based on the segmented device dataset. By way of example, the virtual representation of the medical device including a 2D and/or 3D model of the medical device may be generated and/or derived from the segmented device dataset, for example a contour and/or surface in the segmented device dataset.

This embodiment permits the generation of a realistic virtual representation of the medical device, that may be included into the augmented reality.

According to a further embodiment, the first and second tracking element may be configured as a single sensor. The single sensor may be configured as an electromagnetic and/or optical and/or ultrasound sensor, that may be configured to, for example simultaneously, detect the spatial positionings of the medical device, the first display device and the second display device. For example, the single sensor may be configured to detect and/or track and/or monitor the spatial position and/or orientation of the medical device, the first display device and the second display device in a common coordinate frame.

The single sensor may be arranged spatially apart from any of the devices for which spatial positionings are tracked. Alternatively, the single sensor may be mounted to the first or second display device, that permits an inherent registration between the detected spatial positionings and the display device the single sensor is mounted to.

In an embodiment, the second display device may be at least partially configured as a head-mounted display device that is wearable by a user.

For example, the second display device may be configured as a pair of goggles, for example data goggles, and/or a helmet, for example a data helmet, and/or a screen, and/or projector. When the second display is worn by a user, for example at least partially on the user's head, the second display device will move uniformly with the user, for example the user's head. Since the second display device's spatial positioning may be detected by the second tracking element, the augmented reality, for example the graphical representation of the augmented reality, may be adapted to any changes of the user's positioning, for example the user's head positioning. This permits a continued display of the stereoscopic view of the augmented reality, for example the graphical representation of the augmented reality, to the user. The graphical representation of the augmented reality is immersed into the image data, which image data is displayed by the first display device.

According to a further embodiment, the first and/or second tracking element may include an optical and/or electromagnetic sensor. The sensor may be configured to identify and/or capture and/or spatially locate the device to be detected, for example the medical device and/or the first display device and/or the second display device. The first and/or second tracking element may each include one sensor or multiple sensors, for example multiple sensors of the same or different kind, that may enable a more robust detection of the spatial positioning of the respective device, for example in a medical and/or surgical environment.

By way of example, the optical sensor may include a camera, for example a mono and/or stereo and/or a depth camera, that is configured to detect and/or track and/or monitor the spatial positioning of respective device. The electromagnetic sensor may be configured to detect changes in an electromagnetic field and/or electromagnetic waves caused and/or altered and/or emitted by the respective device to be detected. The ultrasound sensor may be configured to emit and/or receive ultrasound waves that may be emitted and/or deflected and/or altered by the respective device to be detected.

The respective device to be detected, for example the medical device and/or the first display device and/or the second display device, may include a marker element, for example the first marker element and/or the second marker element and/or the third marker element. The optical and/or electromagnetic and/or ultrasound sensor may be configured to identify and/or differentiate and/or detect the respective marker element. This embodiment may provide a precise and reliable detection of the spatial positionings of the medical device and/or the first display device and/or second display device.

According to a further embodiment, the medical device may be configured as an endoscope and/or a catheter and/or a laparoscope.

The medical device may be configured to be at least partially placed inside the region under examination of the subject. The medical device may be configured as a longitudinal diagnostic and/or surgical instrument, that may include an at least partially flexible and/or rigid segment. In addition, the medical device, for example the endoscope and/or catheter and/or laparoscope, may include a lens segment, for example at a proximal portion of the medical device, that may be configured to acquire the image data. For example, the lens segment may include a rod lens.

The medical device may further be configured to be placed and/or moved by a user and/or a robot, for example a catheter robot. In addition, the medical device may be configured to provide an information about its, for example current, characteristic, for example a type and/or operating parameter and/or an acquisition parameter and/or shape and/or penetration depth with regard to the region under examination, to the processing unit of the system. Based thereon, the virtual representation of the medical device may be generated and/or arranged in the augmented reality with higher precision. In addition, the system may be configured to adapt the augmented reality including the graphical representation of the planning dataset based on the characteristic of the medical device, for example an operating parameter and/or an acquisition parameter, such that the graphical representation of the planning dataset matches at least partially with a field-of-view of the medical device.

In an embodiment, the medical device, for example in the embodiment as an endoscope and/or a catheter and/or a laparoscope, may include an angled lens for acquiring the image data. In other words, the field-of-view of the medical device, for example the field-of-view of the angled lens, may be at least partially oriented sideways from a longitudinal direction of the medical device. The angled lens may include an optical element, for example an optical lens and/or an optical fibre, that may be configured to, for example bi-directionally, carry light between the region under examination, for example the field-of-view, and a, for example optical, sensor of the medical device. The sensor may be configured to acquire, for example capture, the image data.

The system may be configured to generate the graphical representation of the planning dataset such that the graphical representation of the planning dataset matches at least partially with the field-of-view of the medical device, for example with the field-of-view of the angled lens.

In cases, where a spatial section around and/or adjacent to a longitudinal path of the medical device is to be imaged by the medical device, an angled lens may enable the medical device to acquire the image data of the spatial section without the need of turning and/or bending the lens segment of the medical device.

Embodiments provide a computer implemented method for generating an augmented reality. In a first step a), a planning dataset is received. In a second step b), image data of a region under examination of a subject is received from a medical device. In a third step c), a graphical representation of the image data is displayed with a first display device. In a fourth step d), a spatial positioning of the medical device is detected with a first tracking element. In a fifth step e), spatial positionings of the first display device and the second display device are detected with a second tracking element.

In a sixth step f), the augmented reality is generated based on the planning dataset and the detected spatial positioning of the medical device. The planning dataset is spatially arranged with respect to the first display device in accordance with the detected spatial positionings of the first and second display device. In a seventh step g), a graphical representation of the augmented reality is displayed with the second display device.

All remarks and advantages laid out above regarding the system for displaying an augmented reality also apply to the method for generating an augmented reality and vice versa. Additional steps or sub-steps may be added regarding additional units according to the described embodiments of the system, that may also be transferred to embodiments of the method for generating an augmented reality and vice versa.

In an embodiment, the augmented reality may be generated including a virtual representation of the medical device based on the detected spatial positioning of the medical device.

The augmented reality may be generated including a 2D and/or 3D arrangement of the planning dataset and the virtual representation of the medical device. The virtual representation of the medical device may include a 2D and/or 3D model of the medical device, that may be generated, for example simulated and/or derived, based on a user input and/or a characteristic and/or an operating parameter and/or an acquisition parameter of the medical device. By way of example, the virtual representation of the medical device may include a volume model, for example a mesh model, and/or a shape model. Alternatively, the virtual representation of the medical device may be selected from a library including virtual representations of different medical devices. The selection may be based on a user input and/or a characteristic of the medical device.

The virtual representation of the medical device may be configured as a realistic and/or simplified, for example abstracted, model of the medical device. A spatial extent and/or shape of the model may at least partially match the spatial extent and/or shape of the medical device. The virtual representation of the medical device may include enhanced geometric features, for example a contour and/or area and/or a longitudinal direction, and/or operating features, for example a planned path and/or a graphical representation of a field-of-view, of the medical device that may improve a visual perception by the user.

The virtual representation of the medical device may be spatially arranged with respect to the planning dataset based on the detected spatial positioning, for example the spatial position and/or spatial orientation, of the medical device. By way of example, this may be implemented by registering the detected spatial positioning of the medical device and the planning dataset in the subject coordinate frame. The augmented reality may depict the virtual representation of the medical device and the graphical representation of the planning dataset in a virtual spatial arrangement, that is in accordance with the real spatial arrangement of the medical device with respect to the region under examination of the subject. The virtual representation of the medical device may be at least partially overlaid and/or integrated with the graphical representation of the planning dataset for generating the augmented reality.

The user may visually perceive the current and/or planned spatial positioning of the medical device with respect to the planning dataset via the augmented reality.

In an embodiment, the execution of steps b) to f) may be repeated when a change in the spatial positioning of the medical device is detected.

A change in the spatial positioning of the medical device may be detected by the first tracking element. For example, the first tracking element may be configured to monitor the spatial positioning of the medical device by either continuously or recurrently detecting the spatial positioning, for example according to a predefined time interval. Further, a difference between the previously and currently detected spatial positioning of the medical device may be computed and compared to a predefined threshold. By way of example, the predefined threshold may be determined via a user input. When the computed difference between the previously and currently detected spatial positioning of the medical device exceeds the predefined threshold, the execution of steps b) to f) may be repeated. By repeating steps b) to f) when a change in the spatial positioning of the medical device is detected, the augmented reality may be generated, for example adapted, such that it depicts the graphical representation of the planning dataset and/or the virtual representation of the medical device in the virtual spatial arrangement in accordance with the real spatial arrangement of the medical device with respect to the region under examination of the subject. Hence, an immersive display of the augmented reality and the image data may be ensured.

In an embodiment, the execution of steps e) to f) may be repeated when a change in the spatial positioning of the first and/or the second display device is detected.

A change in the spatial positioning of the first and/or the second display device may be detected by the second tracking element. For example, the second tracking element may be configured to monitor the spatial positionings of the first and the second display device by either continuously or recurrently detecting the spatial positionings, for example according to a predefined time interval. Further, a difference between the previously and currently detected spatial positioning of the first and/or the second display device may be computed and compared to a predefined threshold. For each of the monitored spatial positionings a particular predefined threshold may be specified, for example via a user input. When the computed difference between the previously and currently detected spatial positioning of the first and/or the second display device exceeds the predefined threshold, the execution of steps e) to f) may be repeated.

The relative spatial positioning between the first and second display device may be monitored by the second tracking element. If the spatial positionings of the first and second display device are equally changing, for example if the relative spatial positioning between the first and second display device remains unchanged, a repeated execution of steps e) to f) may not become necessary. When a change in the relative spatial positioning between the first and second display device is detected by the second tracking element, steps e) to f) may be repeated. Thereby the graphical representation of the augmented reality may be adapted such that it immerses into the graphical representation of the image data displayed by the first display device.

When steps e) to f) are repeated, at least part of the graphical representation of the augmented reality may be adapted such that it spatially and/or visually matches with the graphical representation of the image data, for example an anatomical and/or geometrical feature. The adaption of the at least part of the graphical representation of the augmented reality may include a spatial and/or visual matching of the graphical representation of the augmented reality. The spatial and/or visual matching of the at least part of the graphical representation of the augmented reality may include a rotation and/or translation and/or scaling and/or deformation and/or truncation of the at least part of the graphical representation of the augmented reality based on the detected change in the relative spatial positioning between the first and second display device.

The aforementioned embodiment permits an immersive display of the augmented reality and the image data. For example, when the second display device is configured as a head-mounted display device, steps e) to f) may be repeated whenever a motion of the user's head induces a change in the relative spatial positioning between the first and second display device, for example beyond the predefined threshold.

Embodiments provide a computer program product. The computer program product may include a computer program. The computer program may, for example, be directly loaded into a memory of a processing unit, for example a control device of a medical imaging system, and includes program code to perform the steps of the method according to an embodiment if the computer program is executed in the processing unit. The computer program may be stored on an electronically readably storage medium, that thus includes electronically readable control information stored thereon. The control information includes at least a computer program and is configured such that the control information executes the method when the storage medium is used in a processing unit, for example a control device of a medical imaging system. The electronically readably storage medium may be a non-transient medium, for example a CD-ROM. The computer program product may include further elements, such as a documentation and/or additional components, for example hardware dongles for using the software.

In addition, embodiments may also emanate from an electronically readably storage medium, that stores electronically readable control information such that the control information executes a method according to the invention when the storage medium is used in a processing unit.

A largely software-based implementation bears the advantage that previously used processing units may be easily upgraded via a software update in order to execute a method according to the embodiments.

DETAILED DESCRIPTION

Figure 1:
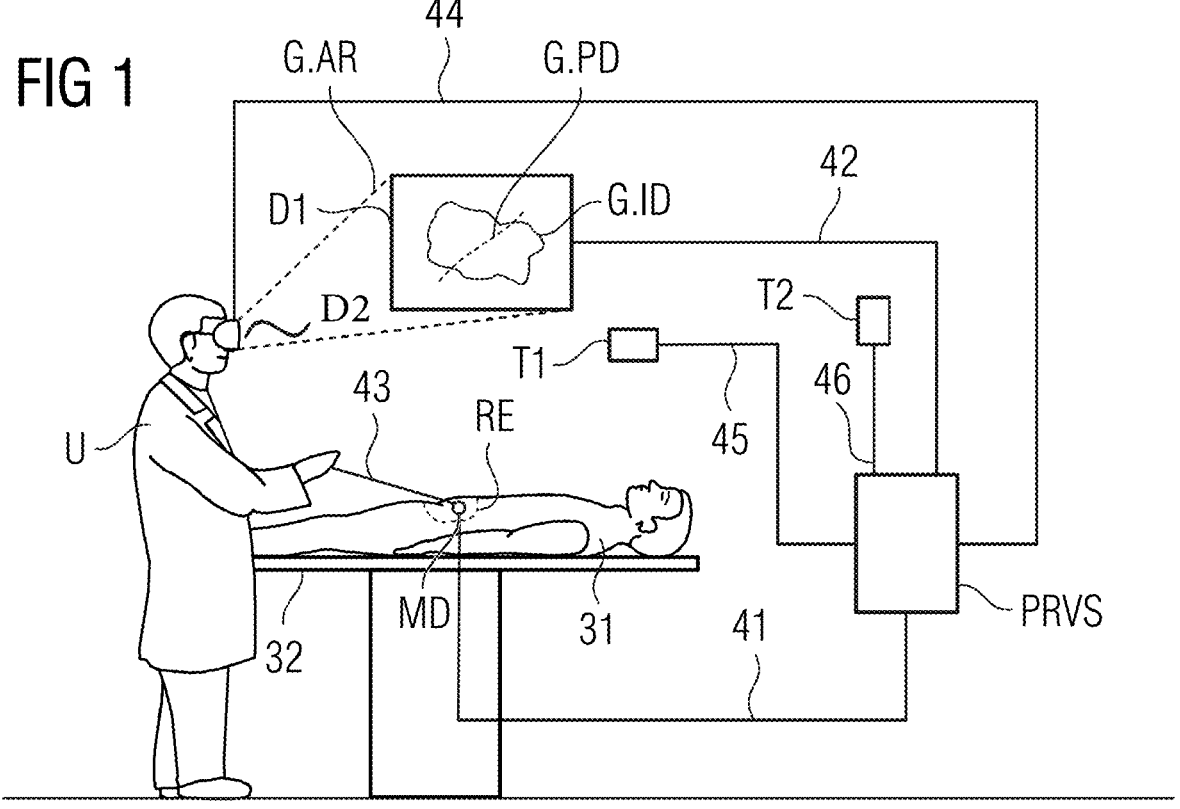
FIGS. 1, 2, and 3 depict schematic representations of different embodiments of a system for displaying an augmented reality.

FIG. 1 depicts a schematic representation of an embodiment of a system for displaying an augmented reality. The system includes a first display device D1, a second display device D2, a first tracking element T1, a second tracking element T2 and a medical device MD. The medical device MD may be configured to acquire image data of a region under examination RE of a subject 31. The subject 31 may be positioned on a patient support 32. The medical device MD may include a diagnostic and/or surgical device that may be configured to acquire, for example intra-procedural and/or real-time, image data of the region under examination RE of the subject 31. For example, the medical device MD may include a catheter and/or endoscope and/or laparoscope, that may be configured to be at least partially placed inside the region under examination RE of the subject 31.

The medical device MD may at least in parts be flexible and/or rigid. The medical device MD may be configured to intra-operatively acquire the image data from the region under examination RE. The medical device MD may include an angled lens for acquiring the image data. The region under examination RE of the subject 31 may include an anatomical region and/or a hollow organ and/or body cavity of the subject 31. The image data may include a 2D and/or 3D representation of at least part of the region under examination RE. In addition, the image data may be time-resolved. The medical device MD may be configured to provide the image data to the first display device D1. For this purpose, the medical device MD may communicate with a processing unit PRVS via a signal 41. The processing unit PRVS may be configured to provide the image data to the first display device D1 via a signal 42.

The first display device D1 may be configured to display a graphical representation of the image data G.ID. For example, the first display device D1 may include a monitor and/or display, that is configured to display the graphical representation of the image data G.ID, for example in real-time. The first display device D1 may include a high-resolution display, for example a 2K-display and/or a 4K-display and/or an 8K-display.

The first tracking element T1 may be configured to detect a spatial positioning of the medical device MD. The first tracking element T1 may include a sensor, exemplary an electromagnetic and/or optical and/or ultrasound sensor, that is configured to detect a spatial positioning of the medical device MD. The first tracking element T1 may be configured to detect and/or track and/or monitor the spatial positioning, for example a spatial position and/or orientation, of the medical device MD, for example in a coordinate frame of the subject 31 and/or a reference coordinate frame. The medical device MD may include a first marker element (not shown), that may be identified and spatially located by the first tracking element T1. The first marker element may be configured as a predefined shape and/or contour and/or segment of the medical device MD, for example a fiducial marker. The first marker element may be configured as at least one marker object that may be attached to the medical device MD, for example on a distal and/or proximal portion of the medical device MD. For example, the first tracking element T1 may include a camera, for example a mono and/or stereo camera, that may be configured to detect and/or track and/or monitor the first marker element. The first tracking element T1 may be configured to provide the detected spatial positioning of the medical device MD to the processing unit PRVS via a signal 45.

The second tracking element T2 may be configured to detect the spatial positionings of the first display device D1 and the second display device D2. The second tracking element T2 may include a sensor, exemplary an electromagnetic and/or optical and/or ultrasound sensor, that is configured to, for example simultaneously, detect a spatial positioning of the first D1 and second display device D2. The second tracking element T2 may be configured to detect and/or track and/or monitor the spatial positioning, for example a spatial position and/or orientation, of the first D1 and second display device D2, for example relative to each other and/or in a common coordinate frame. The second tracking element T2 may be configured to provide the detected spatial positionings of the first D1 and second display device D2 to the processing unit PRVS via a signal 46.

The first display device D1 may include a second marker element (not shown) and/or the second display device D2 may include a third marker element (not shown). The second tracking element T2 may be configured to identify and spatially locate the second and/or the third marker element. The second marker element may be configured as a pre-defined shape and/or contour and/or segment of the first display device D1, for example a fiducial marker. The second marker element may be configured as at least one marker object that may be attached to the first display device D1. Analogously, the third marker element may be configured as a predefined shape and/or contour and/or segment of the second display device D2, for example a fiducial marker. The third marker element may be configured as at least one marker object that may be attached to the second display device D2.

The second tracking element T2 may be configured to detect a relative and/or absolute spatial positioning between the first and second display device. The second tracking element T2 may include a camera, for example a mono and/or stereo camera, that is configured to detect and/or track and/or monitor the second and/or the third marker element.

The system, for example the processing unit PRVS, may be configured to receive a planning dataset. The planning dataset may include a, for example pre-procedural, 2D and/or 3D representation of at least part of the region under examination RE of the subject 31. In addition, the planning dataset may be time-resolved. The planning dataset may include pre-processed information, for example annotations and/or anatomical landmarks and/or geometrical landmarks and/or enhanced features. In addition, the planning dataset may include planning information regarding a path for the medical device MD and/or information regarding a treatment plan.

The system may be configured to segment at least part of the planning dataset and to generate the augmented reality based on the segmented planning dataset.

The system may be configured to generate the augmented reality based on the planning dataset and the detected spatial positioning of the medical device MD. The planning dataset may be spatially arranged with respect to the first display device D1 in accordance with the detected spatial positionings of the first D1 and second display device D2. In addition, the second display device D2 may be configured to display a graphical representation of the augmented reality G.AR.

The second display device D2 may include a second display interface, that may be configured to receive the augmented reality, for example via a signal 44 from the processing unit PRVS. For example, the second display device D2 may be configured as a pair of goggles, for example data goggles, and/or a helmet, for example a data helmet, and/or a screen and/or projector, that is wearable by the user U. When the second display device D2 is worn by the user U, for example at least partially on the user's head, the second display device D2 will move uniformly with the user U, for example the user's head. Hereby, the user U may perceive the graphical representation of the augmented reality G.AR and simultaneously control and/or actuate and/or position the medical device MD, for example via a control interface 43. The control interface 43 may be located at a distal portion of the medical device MD.

The second tracking element T2 may be arranged spatially apart from the first D1 and second display device D2. The first T1 and second tracking element T2 may be configured as a single sensor (not shown).

In addition, the system may be configured to monitor at least one of the detected spatial positionings and adapt the augmented reality when a change in the at least one of the detected spatial positionings occurs.

Figure 2:
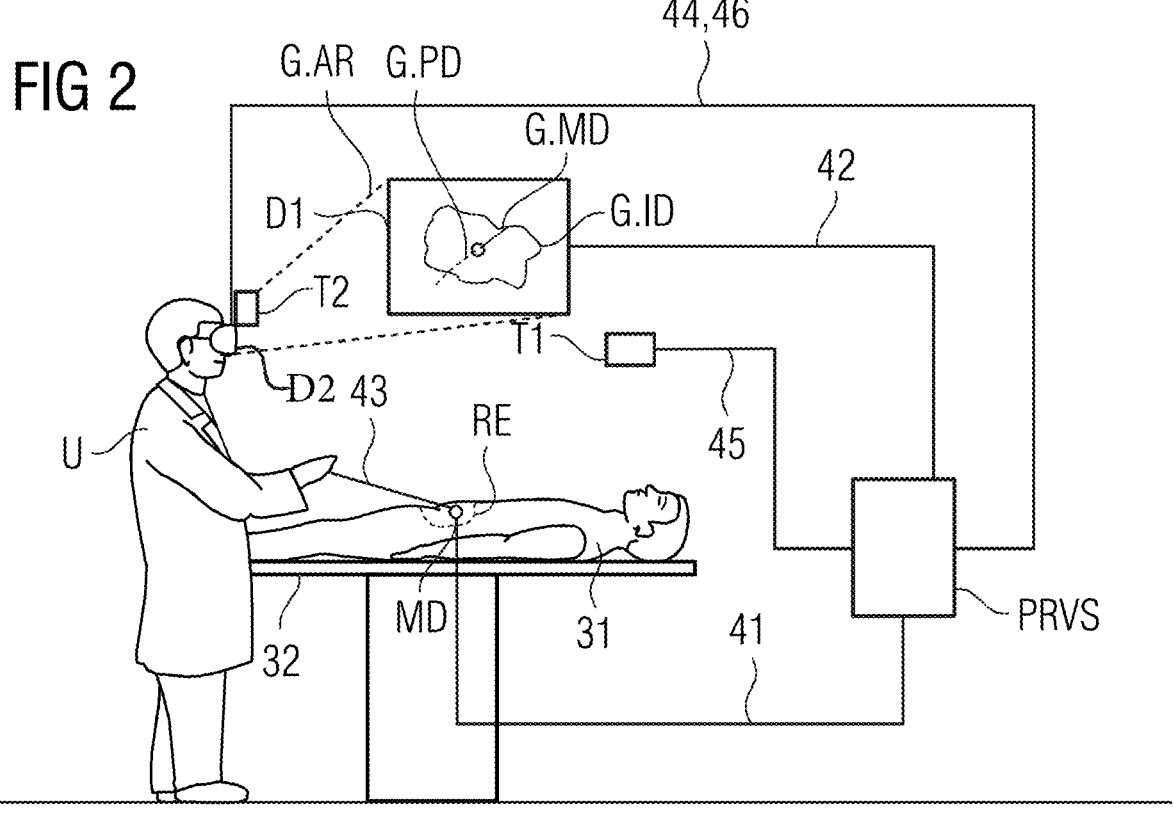

FIG. 2 depicts another embodiment of a system for displaying an augmented reality. The system may be configured to generate the augmented reality including a virtual representation of the medical device G.MD based on the detected spatial positioning of the medical device MD. The graphical representation of the augmented reality G.AR may include depth cue information with regard to the planning dataset and/or the virtual representation of the medical device G.MD.

The second tracking element T2 may be mounted, for example attached, to the second display device D2 in a predefined position, for example a fixed position with respect to the second display device D2. The second tracking element T2 may be mounted to the second display device D2 such that a spatial detection range of the second tracking element T2 at least partially coincides with a field-of-view of the user U. Thereby, it may be ensured, that the relative spatial positioning between the first D1 and second display device D2 may be detected by the second tracking element T2 whenever the user U turns its field-of-view towards the first display device D1.

Figure 3:
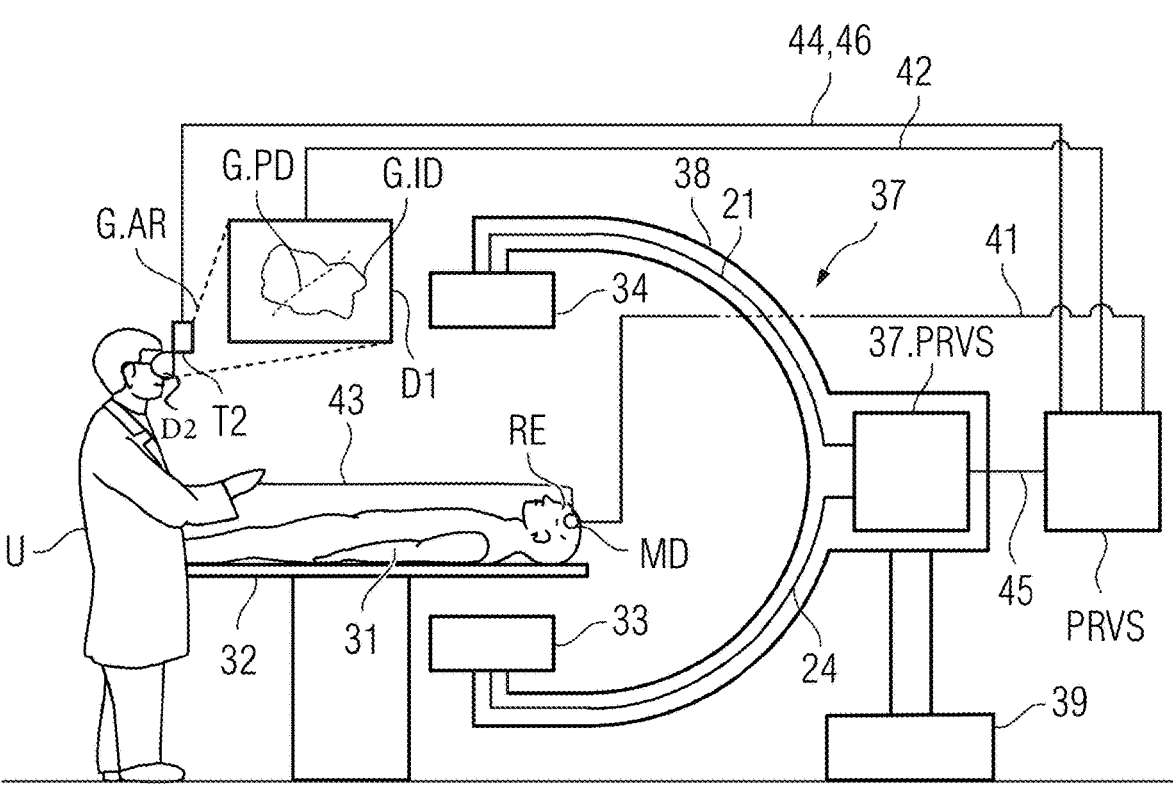

FIG. 3 depicts another embodiment of a system for displaying an augmented reality. The first tracking element T1 may be configured as a medical imaging system, for example a medical C-arm X-ray system 37.

The medical C-arm X-ray system 37 may be configured to, for example recurrently and/or continuously, acquire further medical image data of the region under examination RE and to detect the spatial positioning of the medical device MD based on the further medical image data.

When the first tracking element T1 is configured as a medical C-arm X-ray system 37 and the planning dataset was acquired by that medical C-arm X-ray system 37, the detected spatial positioning of the medical device MD may inherently be registered to the planning dataset. The medical C-arm X-ray system 37 may include a further processing unit 37.PRVS, that may be in communication with the processing unit PRVS via the signal 45. The medical C-arm X-ray system 37 may further include an X-ray detector unit 34 and an X-ray source 33, that may be mounted to the C-arm 38 of the C-arm X-ray system 37 such that they are movable around at least one axis. In addition, the medical C-arm X-ray system 37 may include a motion unit 39, for example including at least a wheel and/or rail and/or robotic system, that permits a spatial motion of the medical C-arm X-ray system 37.

For the acquisition of the further medical image data and/or the planning dataset, for example including at least one projection image of the region under examination RE of the subject 31, the further processing unit 37.PRVS may send a signal 24 to the X-ray source 33. Consequently, the X-ray source 33 may emit an X-ray bundle, for example a cone-beam and/or a fan-beam and/or a parallel-beam. When the X-ray bundle impinges on a surface of the X-ray detector unit 34 after an interaction between the X-ray bundle and the region under examination RE of the subject 31, the X-ray detector unit 34 may send a signal 21 to the further processing unit 37.PRVS. Based on the signal 21 the further processing unit 37.PRVS may be configured to receive the further medical image data and/or the planning dataset. The further processing unit 37.PRVS may provide the further medical image data and/or the planning dataset and/or the spatial positioning of the medical device MD to the processing unit PRVS via the signal 45.

The medical C-arm X-ray system 37 may be configured to acquire a device dataset. The system, for example the processing unit PRVS and/or the further processing unit 37.PRVS, may be configured to segment the medical device MD in the device dataset and to generate the virtual representation of the medical device G.MD based on the segmented device dataset.

Figure 4:
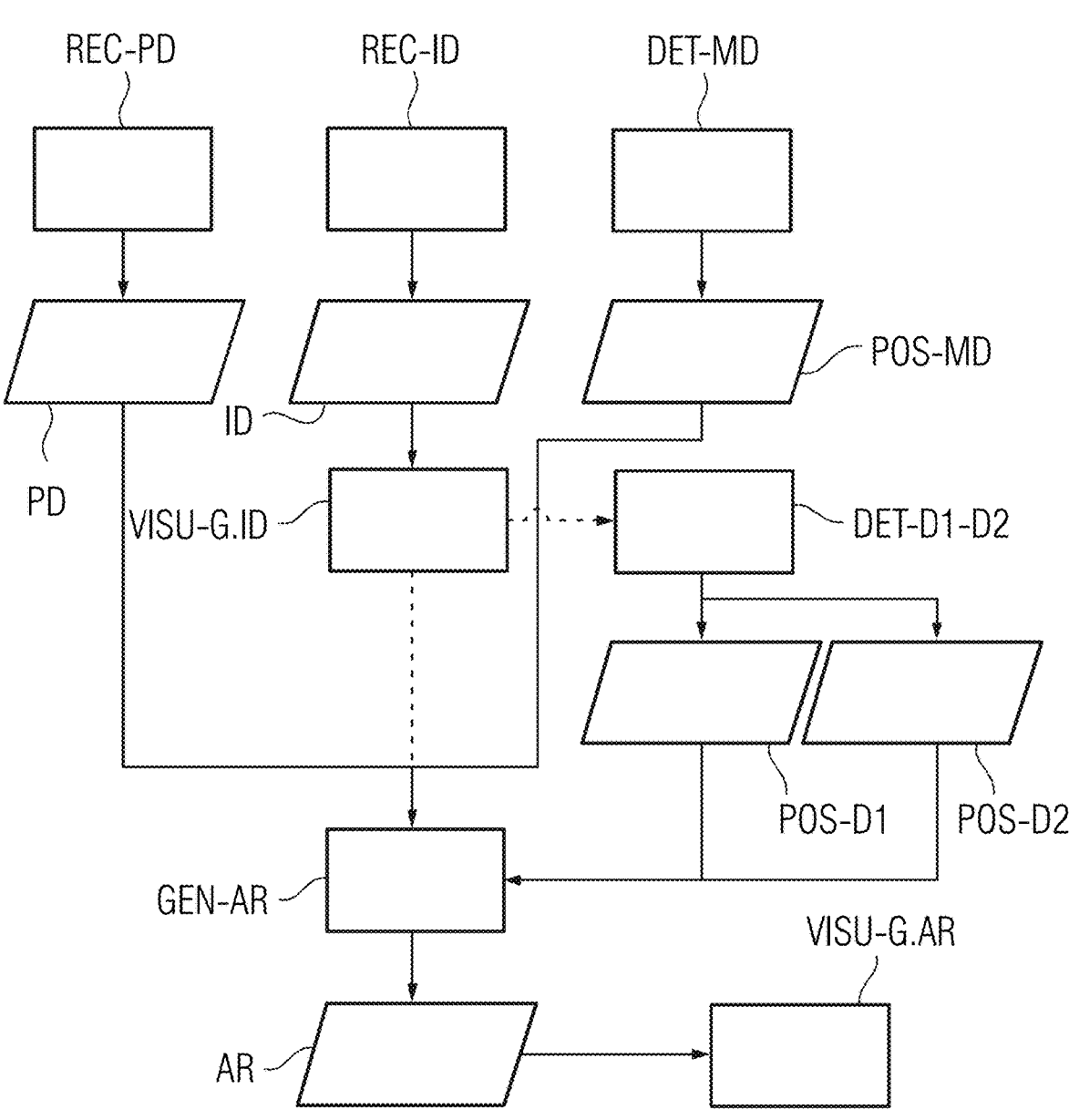
FIGS. 4, 5, 6, and 7 depict schematic representations of different embodiments of a method for generating an augmented reality.

FIG. 4 depicts a schematic representation of an embodiments of a method for generating an augmented reality. In a first step a), the planning dataset PD may be received REC-PD. In a second step b), the image data ID of the region under examination RE of the subject 31 may be received REC-ID from the medical device MD. In a third step c), the graphical representation of the image data G.ID may be displayed VISU-G.ID with the first display device D1. In a fourth step d), the spatial positioning of the medical device POS-MD may be detected DET-MD with the first tracking element T1. In a fifth step e), the spatial positionings of the first display device POS-D1 and the second display device POS-D2 may be detected DET-D1-D2 with the second tracking element T2. In a sixth step f), the augmented reality AR may be generated GEN-AR based on the planning dataset PD and the detected spatial positioning of the medical device POS-MD. The planning dataset PD may be spatially arranged with respect to the first display device D1 in accordance with the detected spatial positionings of the first POS-D1 and second display device POS-D2. In a seventh step g), a graphical representation of the augmented reality G-AR may be displayed VISU-G.AR with the second display device D2.

Figure 5:
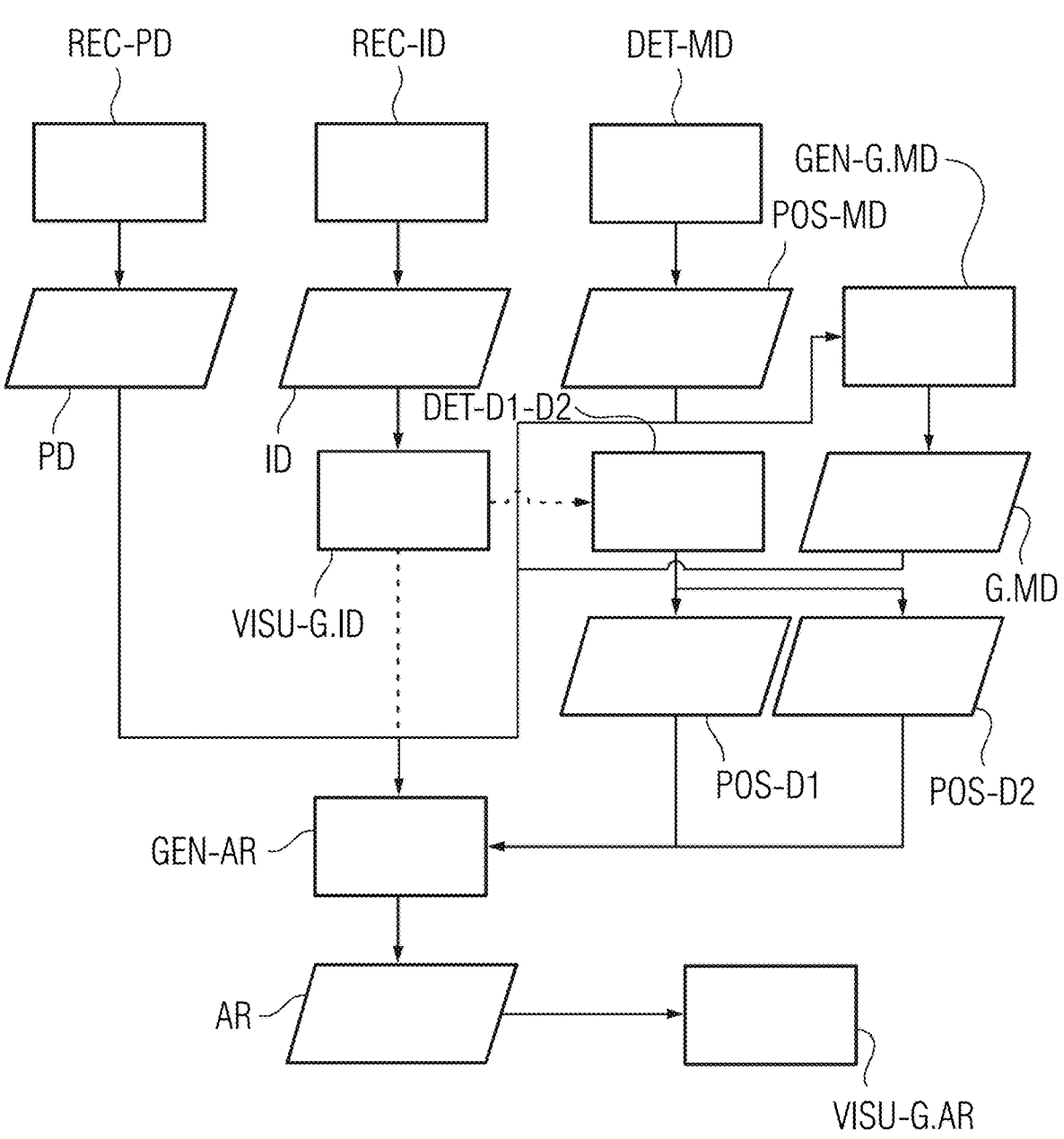

FIG. 5 shows another embodiment of the method for generating an augmented reality. The augmented reality AR may be generated GEN-AR including a virtual representation of the medical device G.MD based on the detected spatial positioning of the medical device POS-MD.

Figure 6:
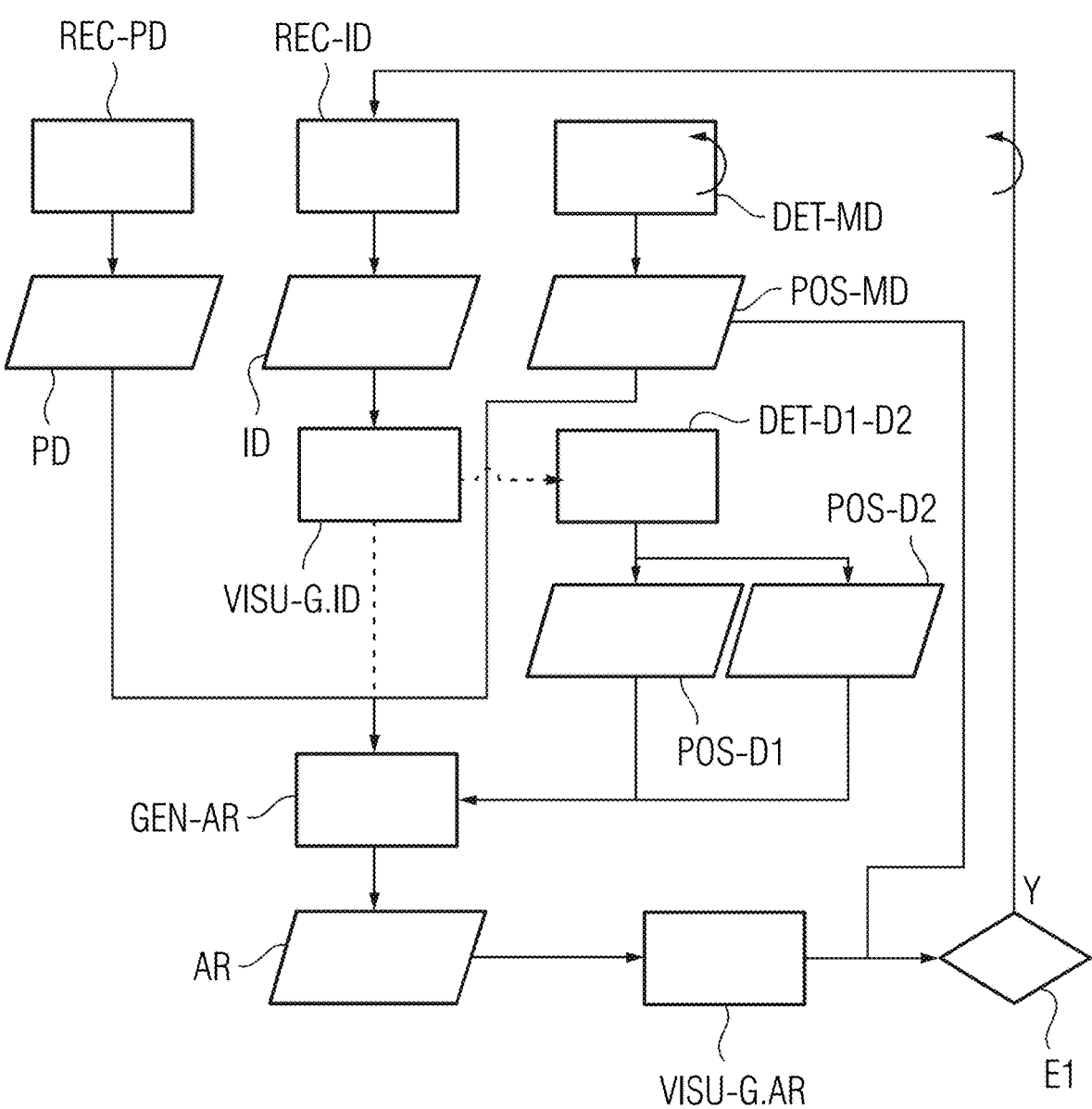

FIG. 6 shows another embodiment of the method for generating an augmented reality. The execution of steps b) to f) may be repeated when a change in the spatial positioning of the medical device POS-MD is detected DET-MD. A change in the spatial positioning of the medical device POS-MD may advantageously be detected DET-MD by the first tracking element T1. For example, the first tracking element T1 may monitor the spatial positioning of the medical device POS-MD by either continuously or recurrently detecting the spatial positioning POS-MD, for example after a predefined time interval. Further, a difference between the previously and currently detected spatial positioning of the medical device POS-MD may be computed and compared E1 to a predefined threshold. When the computed difference between the previously and currently detected spatial positioning of the medical device POS-MD exceeds Y the predefined threshold, the execution of steps b) to f) may be repeated.

Figure 7:
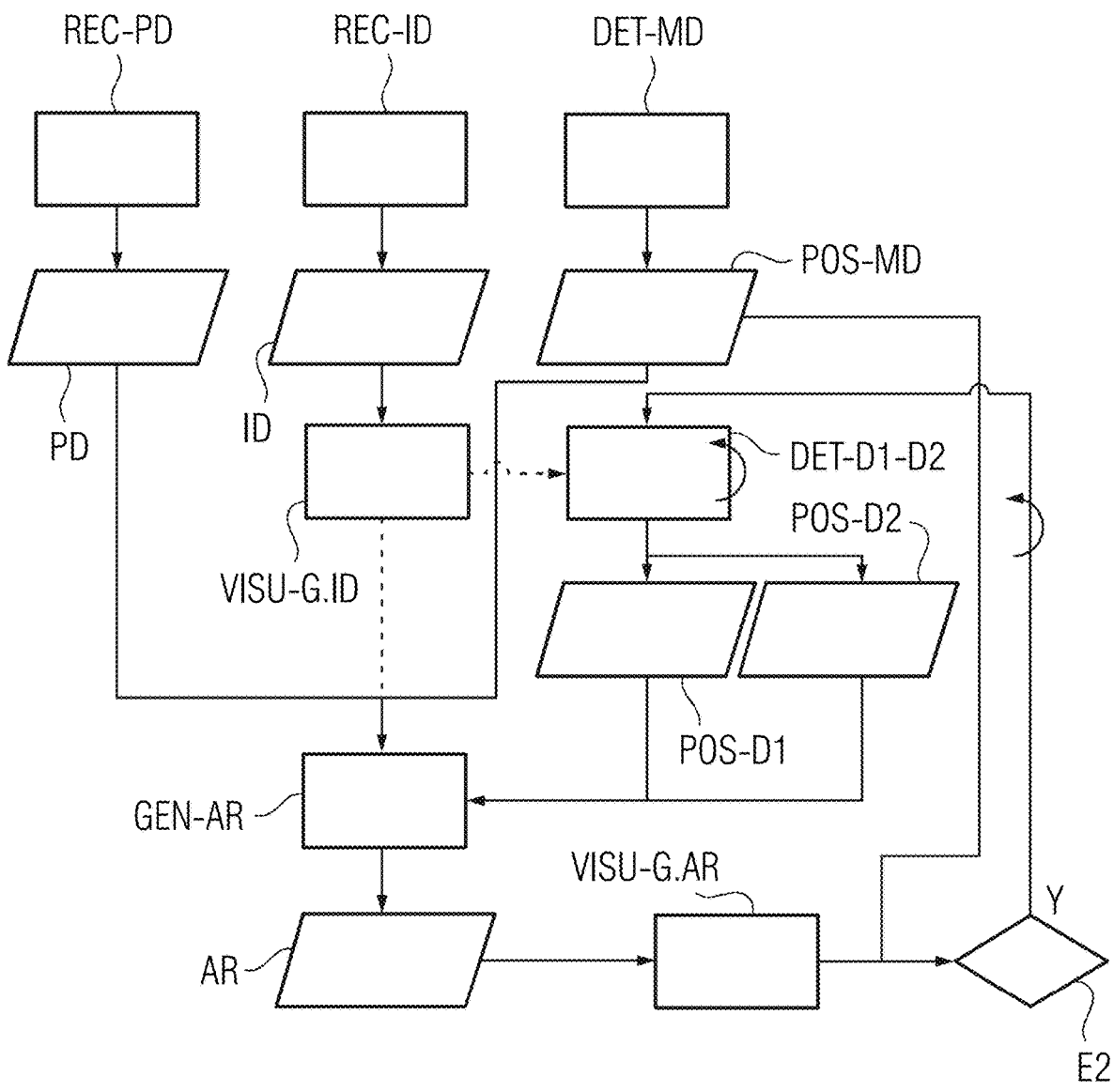

FIG. 7 shows another embodiment of the method for generating an augmented reality. The execution of steps e) to f) may be repeated when a change in the spatial positioning of the first display device POS-D1 and/or the spatial positioning of the second display device POS-D2 is detected. A change in the spatial positioning of the first POS-D1 and/or the second display device POS-D2 may advantageously be detected DET-D1-D2 by the second tracking element T2. For example, the second tracking element T2 may monitor the spatial positionings of the first POS-D1 and the second display device POS-D2 by either continuously or recurrently detecting the spatial positionings DET-D1-D2, for example after a predefined time interval. Further, a difference between the previously and currently detected spatial positionings of the first POS-D1 and/or the second display device POS-D2 may be computed and compared E2 to a predefined threshold. When the computed difference between the previously and currently detected spatial positionings of the first POS-D1 and/or the second display device POS-D2 exceeds Y the predefined threshold, the execution of steps e) to f) may be repeated.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present disclosure has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A system for displaying an augmented reality the system comprising:

a medical device configured to acquire image data of a region under examination of a subject and provide the image data to a first display device;

the first display device configured to display a graphical representation of the image data;

a second display device configured to display a graphical representation of the augmented reality;

a first tracking element configured to detect a spatial positioning of the medical device;

a second tracking element configured to detect spatial positionings of the first display device and the second display device;

a controller configured to:

receive a planning dataset; and generate the augmented reality based on the planning dataset and the detected spatial positioning of the medical device, wherein in the augmented reality the planning dataset is spatially arranged with respect to the first display device in accordance with the detected spatial positionings of the first display device and the second display device, wherein the graphical representation of the augmented reality that is displayed by the second display device is at least partially overlaid and/or integrated into the graphical representation of the image data that is displayed by the first display device.

2. The system of claim 1, characterized in that the controller is further configured to generate the augmented reality comprising a virtual representation of the medical device based on the detected spatial positioning of the medical device.

3. The system of claim 1, wherein the controller is further configured to:

monitor at least one of the detected spatial positionings; and adapt the augmented reality when a change in the at least one of the detected spatial positionings occurs.

4. The system of claim 1, wherein the second tracking element is mounted to the second display device in a predefined position.

5. The system of claim 1, wherein the second tracking element is arranged spatially apart from the first display device and second display device.

6. The system of claim 1, wherein the controller is further configured to:

segment at least part of the planning dataset; and generate the augmented reality based on the segmented planning dataset.

7. The system of claim 1, wherein the first tracking element is configured as a medical imaging system.

8. The system of claim 7, wherein the medical imaging system is configured to acquire a device dataset, wherein the controller is further configured to:

segment the medical device in the device dataset; and generate the virtual representation of the medical device based on the segmented device dataset.

9. The system of claim 1, wherein the second display device is at least partially configured as a head-mounted display device which is wearable by a user.

10. The system of claim 1, wherein the medical device is configured as an endoscope, a catheter, or a laparoscope, wherein the medical device comprises an angled lens for acquiring the image data.

11. A method for generating an augmented reality, the method comprising:

receiving a planning dataset;

receiving image data of a region under examination of a subject from a medical device;

displaying a graphical representation of the image data with a first display device;

detecting a spatial positioning of the medical device with a first tracking element;

detecting spatial positionings of the first display device and a second display device with a second tracking element;

generating the augmented reality based on the planning dataset and the detected spatial positioning of the medical device, wherein the planning dataset is spatially arranged with respect to the first display device in accordance with the detected spatial positionings of the first display device and second display device; and displaying a graphical representation of the augmented reality with the second display device, wherein the graphical representation of the augmented reality that is displayed by the second display device is at least partially overlaid and/or integrated into the graphical representation of the image data that is displayed by the first display device.

12. The method of claim 11, wherein the augmented reality is generated comprising a virtual representation of the medical device based on the detected spatial positioning of the medical device.

13. The method of claim 11, wherein receiving image data, displaying, detecting, detecting, and generating is repeated when a change in the spatial positioning of the medical device is detected.

14. The method of claim 11, wherein detecting spatial positionings and generating is repeated when a change in the spatial positioning of the first display device, the second display device, or the first display device and the second display device is detected.

15. A non-transitory computer implemented storage medium that stores machine-readable instructions executable by at least one processor to generate an augmented reality, the machine-readable instructions comprising:

receiving a planning dataset;

receiving image data of a region under examination of a subject from a medical device;

displaying a graphical representation of the image data with a first display device;

detecting a spatial positioning of the medical device with a first tracking element;

detecting spatial positionings of the first display device and a second display device with a second tracking element;

generating the augmented reality based on the planning dataset and the detected spatial positioning of the medical device, wherein the planning dataset is spatially arranged with respect to the first display device in accordance with the detected spatial positionings of the first display device and second display device; and displaying a graphical representation of the augmented reality with the second display device, wherein the graphical representation of the augmented reality that is displayed by the second display device is at least partially overlaid and/or integrated into the graphical representation of the image data that is displayed by the first display device.

16. The non-transitory computer implemented storage medium of claim 15, wherein the augmented reality is generated comprising a virtual representation of the medical device based on the detected spatial positioning of the medical device.

17. The non-transitory computer implemented storage medium of claim 15, wherein receiving image data, displaying, detecting, detecting, and generating is repeated when a change in the spatial positioning of the medical device is detected.

18. The non-transitory computer implemented storage medium of claim 15, wherein detecting spatial positionings and generating is repeated when a change in the spatial positioning of the first display device, the second display device, or the first display device and the second display device is detected.

* * * * *